United States Patent [19]

Edwards

[11] Patent Number: 5,700,346
[45] Date of Patent: Dec. 23, 1997

[54] AUTOMATED SLIDE STAINING SYSTEM

[76] Inventor: Peter S. Edwards, 2464 Elfinwing La., Tallahassee, Fla. 32308

[21] Appl. No.: 277,170

[22] Filed: Jul. 19, 1994

[51] Int. Cl.$^6$ ..................................... B05B 12/02
[52] U.S. Cl. ................. 156/357; 156/364; 156/556; 156/570; 118/326; 118/401; 118/425
[58] Field of Search ................. 118/58, 64, 326, 118/401, 425; 156/356, 357, 360, 578, 363, 364, 556, 570; 221/36, 58, 59

[56] References Cited

U.S. PATENT DOCUMENTS

| | | | |
|---|---|---|---|
| 3,431,886 | 3/1969 | McCormick | 118/401 X |
| 3,823,845 | 7/1974 | Mott, Sr. et al. | 211/59 |
| 3,892,197 | 7/1975 | Kinney et al. | 118/50 X |
| 3,903,908 | 9/1975 | Logue et al. | 118/425 X |
| 3,939,019 | 2/1976 | Pickett | 156/57 |
| 4,092,952 | 6/1978 | Wilkie et al. | 118/58 |
| 4,151,809 | 5/1979 | Johnson | 118/401 X |
| 4,190,472 | 2/1980 | Slonicki | 156/57 |
| 4,537,648 | 8/1985 | Shiino et al. | 156/351 |
| 4,651,671 | 3/1987 | Pedersen | 118/57 |
| 4,738,824 | 4/1988 | Takeuchi | 118/425 X |
| 4,936,465 | 6/1990 | Zold | 209/3.1 |

Primary Examiner—David A. Simmons
Assistant Examiner—Paul M. Rivard
Attorney, Agent, or Firm—Carnes, Corra and Dixon

[57] ABSTRACT

The present invention provides an automatic slide staining system which will process stained slides, such as cytology or histology specimens. The present invention includes two embodiments for the staining system. The first system includes a slide storage device, a slide transport apparatus, a first platen including a plurality of staining stations, a heating station, and a housing. In order to utilize the first embodiment of the system of the present invention, the stained slides are placed in the storage device. The slides are removed from the storage device and are processed on the various stations via the transport apparatus. The first system can be altered slightly so that a cover slip apparatus can be incorporated within the system. In order to do so, the heating station is removed. A cover slip dispensing apparatus replaces the heating station. This will permit for a cover slip to be placed on the stained slide after a complete transverse of the slide staining stations.

28 Claims, 6 Drawing Sheets

AUTOMATED SLIDE STAINING SYSTEM

BACKGROUND OF THE INVENTION

1. Field of the Invention

The present invention relates to a system for staining slides of human tissue specimens, and more particularly for staining histology and cytology tissue specimens on a slide for subsequent microscopic examination.

2. Description of the Background Art

Throughout the United States steps are being taken to improve Slide Staining Systems for subsequent pathologic examination in medical laboratories and hospitals. The primary cost component of preparing and staining a slide is labor. Accordingly, many efforts have been devoted to reduce the labor cost component of preparing a slide. With the advent of cost containment throughout the health-care industry, renewed efforts are being made to examine all direct labor cost areas with a focus on reducing the amount of labor heretofore involved, and the associated cost.

For example, U.S. Pat. No. 4,190,472 issued to Slonicki, discloses an automated system for the application of cover glasses on histological and cytological slides. Patent '472 discloses a processing area wherein a slide that has been stained previously is progressively turned 90 degrees to mate with a cover glass to insure a contamination free tissue specimen. Patent '472 also disclosed a device for depositing glue on the stain slide and a device for applying the cover glass to the glued portion of the slide. Patent 472 is silent of the use of a fume extractor to remove noxious and harmful fumes from the apparatus which could cause a reduction in the quality of the surrounding environment, where other lab personnel are working.

U.S. Pat. No. 3,939,019 issued to Pickett disclosed an apparatus for covering a slide with a tape material. Patent 019 teaches away from the use of a cover glass to seal the specimen and maintain the specimen in a contamination free environment.

U.S. Pat. No. 4,936,465 issued to Zold discloses an apparatus for dispensing a staining fluid. Patent 465 does not teach or suggest using the apparatus for sealing the stained slide with any type of optically correct transparent material. Patent 465 further is silent to the use of a fume extractor for cleaning the toxic and noxious gases generated in the staining process and removing potentially harmful compounds from the environment which could be harmful to laboratory workers who are adjacent to or in proximity to the slide staining apparatus.

None of these previous efforts, however, provide the benefits intended with the present invention. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention provides an automatic slide staining system which will process stained slides, such as cytology or histology specimens. The present invention includes two embodiments for the staining system.

The first system includes a slide storage device, a slide transport apparatus, a first platen including a plurality of staining stations, a heating station, and a housing. In order to utilize the first embodiment of the system of the present invention, the stained slides are placed in the storage device. The storage device is adapted to be removably secured to a shaft located at one end of the first platen. A transport system enables the slides to be released from the storage device and carried onto the staining stations.

The last dispensing station on the first platen releases a resin solution. From the last dispensing station, the slide is guided to a heating station. At this time the resin coating, which was applied at the last dispensing station, is dried. This will provide for the slide to have a protective resin coating. After the resin has dried, the slide will be dropped into a slide receptacle.

The first embodiment can be altered slightly so that a cover slip apparatus can be incorporated within the system. In order to do so, the heating station is removed. A cover slip dispensing apparatus replaces the heating station. The cover slip apparatus used in this embodiment includes a storage and dispensing box, a second platen, and rollers placed therebetween. The cover slips are maintained and removed from the storage and dispensing box to the second platen via the rollers. A transport system, located along the sides of the second platen, permits for the cover slip to be guided on the second platen.

The second platen includes a first end, a middle area, and a second end. The first end of the second platen is at an obtuse angle with respect to the middle area. The first platen contacts the middle area of the second platen. This configuration will permit for the cover slip to contact and adhere to the stained slide at the middle area of the second platen. A pressure roller, located above the second platen, applies a sufficient amount of force on the slide to ensure that the cover slip will adhere to the slide. After the cover slip is completely secured to the slide, it will be transported to a holding receptacle located at the second end of the platen.

Accordingly, it is the object of the present invention to provide for a staining system that will process stained slides efficiently and effectively.

It is another object of the present invention to provide for a staining system that will process stained slides and encapsulate the specimen on a slide in a sterile and contaminant free environment.

It is a further object of the present invention to stain the slide and encapsulate the slide in a contamination free environment using minimal laboratory labor.

It is still a further object of the present invention to provide a slide staining system that removes all the toxic and noxious fumes generated in the slide staining process from the surrounding environment in order to reduce the adverse effect on laboratory personnel.

It is yet another object of the present invention to provide a slide staining system that can quickly be converted from histological specimens to cytological specimens with a minimum of downtime and minimum of conversion effort.

It is yet a further object of the present invention to provide a slide staining system that eliminates any potential for cellular contamination between slides during the staining process.

It is another object of the present invention to provide a slide staining system wherein the human cell tissue specimens are never in direct communication with the slide staining apparatus to prevent any cross contamination of human cell specimens between successive slides.

A final object of the present invention, to be specifically enumerated herein, is to provide a slide staining system in accordance with the proceeding objects and which will conform to conventional forms of manufacture, be of simple construction and easy to use so as to provide a device that would be economically feasible, long lasting and relatively trouble free in operation.

Although there have been many inventions related to a slide staining system none of the inventions have become sufficiently compact, low cost and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, other objects and a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

Similar reference numerals refer to similar parts throughout the several views of the drawings.

DESCRIPTION OF THE PREFERRED EMBODIMENTS

Figure 1:
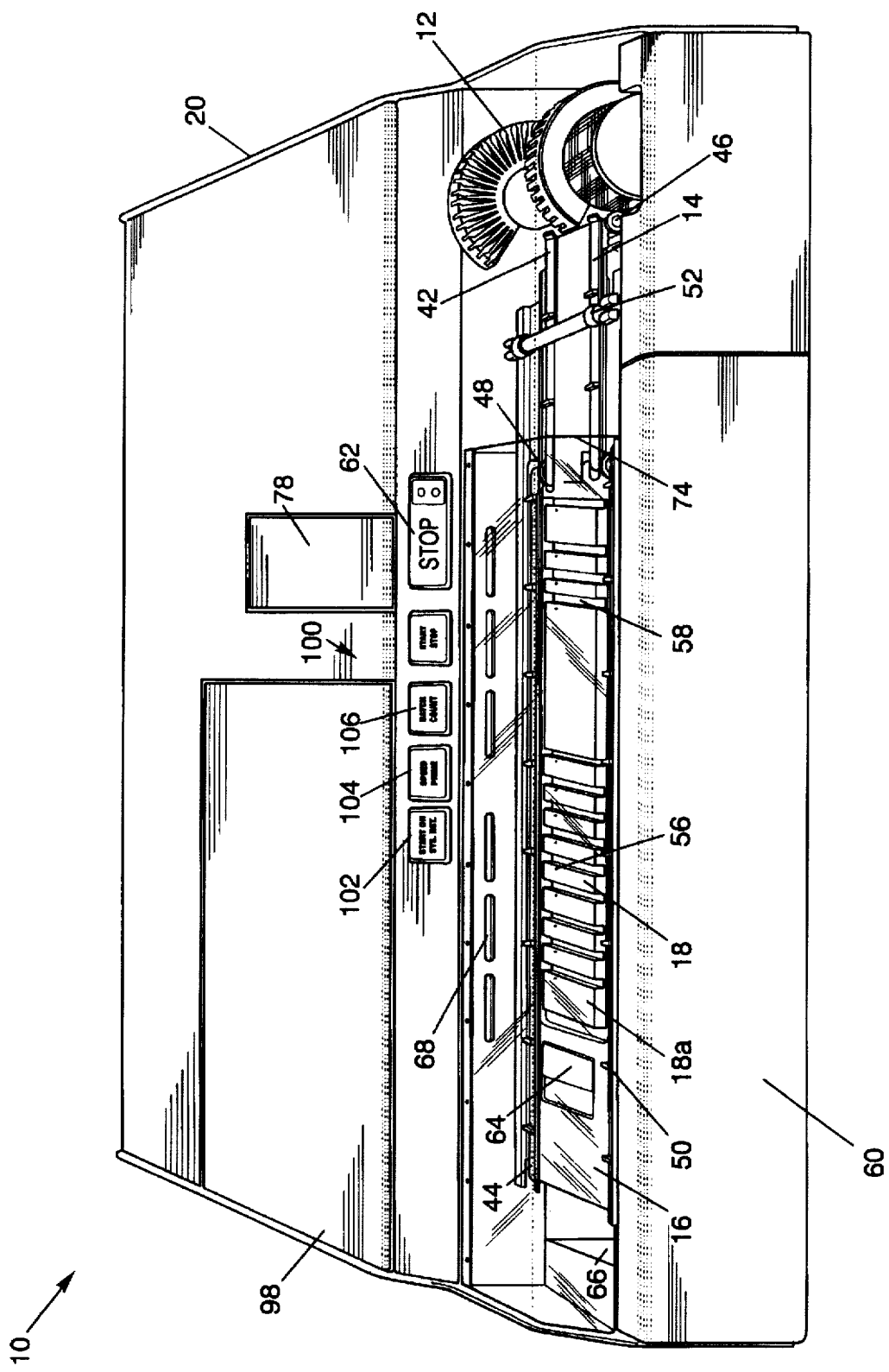
FIG. 1 is a perspective view of the automated slide staining system of the present invention.
Figure 2:
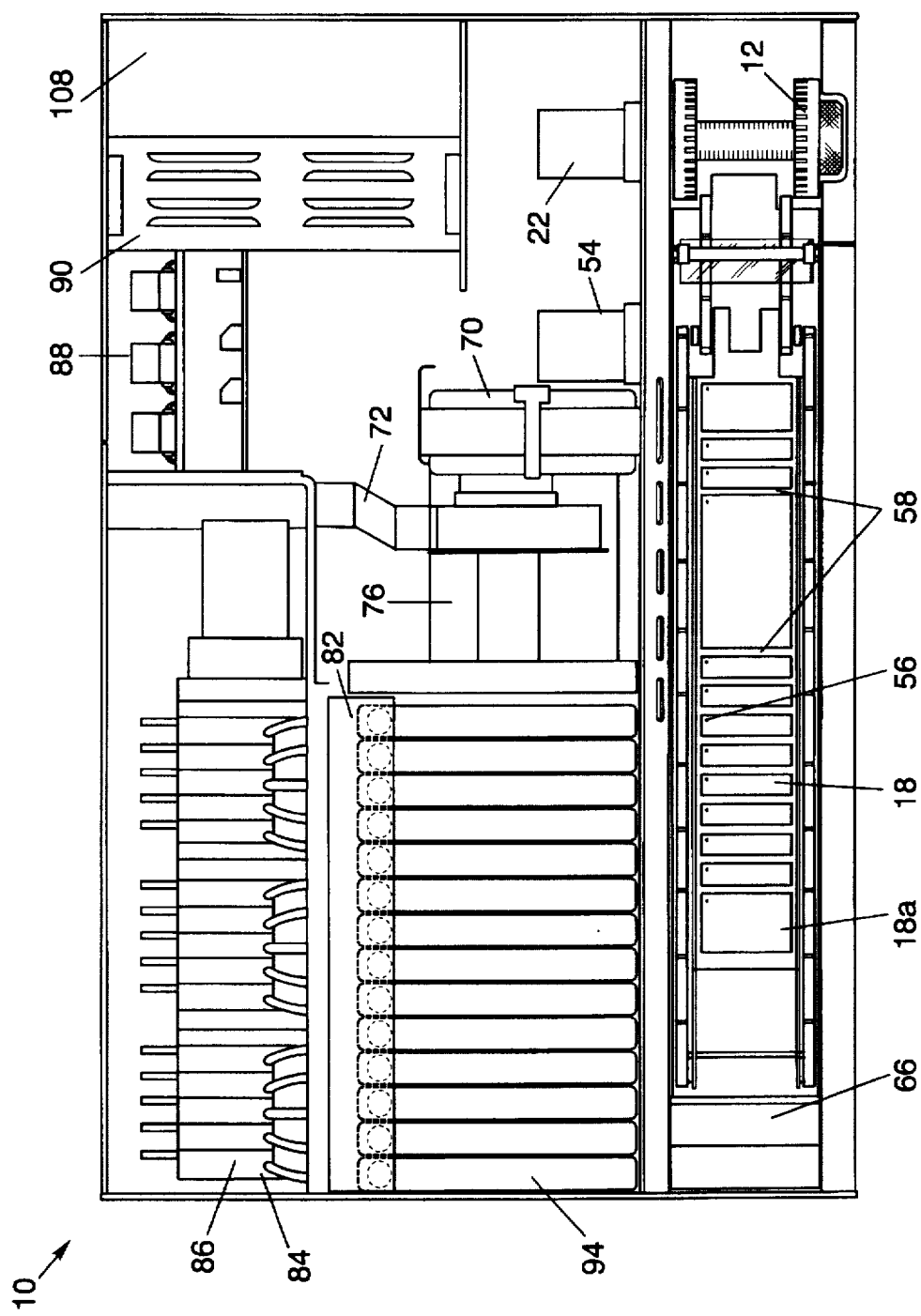
FIG. 2 is a top view of the automated slide staining system of the present invention.

FIGS. 1 and 2 illustrate the various views of the first embodiment of the automatic slide staining system of the present invention. As seen in these figures, the automatic slide staining system 10 consists of a slide storage device 12, a slide transport apparatus 14, a first platen 16 including a plurality of staining stations 18, and a housing 20.

Stained slides (not illustrated), such as cytology or histology specimens, are inserted into the slide storage device or carousel. This carousel 12 is removably secured to a shaft (not illustrated) of a first motor (stepper motor) 22. Once the machine is activated, the first motor is initiated to provide for the shaft to rotate. The slides are then individually discharged onto slide transport apparatus in order to be processed on the various stations.

Figure 3:
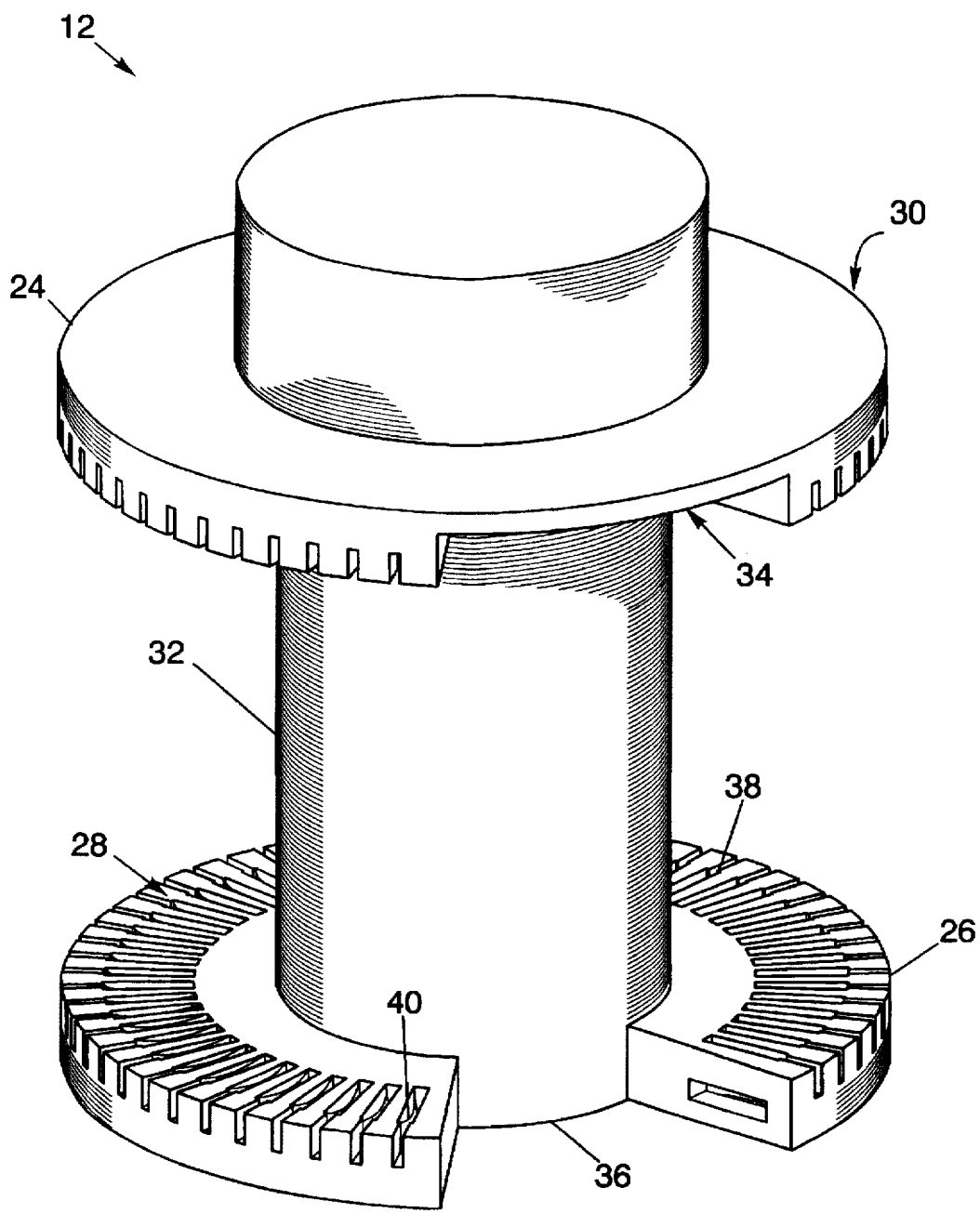
FIG. 3 is a perspective view of the slide storage device used in the staining system of the present invention.

The carousel, as illustrated in these drawings and in further detail in FIG. 3, has an upper portion 24 and a lower portion 26. The upper and lower portions are identical in size.

The upper and lower portions each have an inner surface 28 and an outer surface 30. The inner surface of the upper portion faces the inner surface of the lower portion. Centrally located in each of the portions is an aperture (not illustrated).

Located between the upper and lower portion is a hollow rod 32. The rod has a first end 34 and a second end 36. The first and second ends are received in the apertures which are located in the upper and lower portion, respectively. The shaft of the first motor on the staining apparatus receives the hollow rod. This provides for the slide storage device to have a horizontally disposed central axis once it is secured to the shaft.

A plurality of radially oriented walls are provided along the inner surface of the upper and lower portion. These walls form a plurality of compartments 38. A retainer spring 40 is oriented between two adjacent walls for permitting releasable securement of the slide within the compartment. This retainer spring will permit for the carousel to accept slides of arbitrary thickness.

The slides are released one at a time from the storage device and onto the first platen 16 via a slide transport apparatus 14. This slide transport apparatus consists of a first pair of conveyor belts 42 and a second pair of conveyor belts 44.

The design and structure of the conveyor belts permit a means of releasing the stained slides from the carousel and a means of transporting the slides to the various stations.

The first pair 42 of conveyor belts are parallel to each other and are located between the carousel and staining stations.

The second pair 44 of conveyor belts are parallel to each other and are located below and along the sides of the processing stations.

The first pair of conveyer belts extend around a first pulley 46 and a second pulley 48 (partly illustrated). The second pair of conveyor belts extend around a third pulley and a fourth pulley (neither illustrated). The first pulley is located within the housing and is in the proximity of the carousel. The second pulley is located within the housing and is in the proximity of the first staining station. The third pulley is located next to the second pulley and the fourth pulley is located at the far end of the first platen.

The conveyor belts further include a plurality of evenly spaced rods or pips 50 which protrude vertically and beyond the processing stations. The rods or pips in each pair of belts are in co-alignment. Once the apparatus is activated, the belts start to rotate about the pulleys. This provides for the rods or pips from the first pair of belts to push on the edge of a slide in the carousel. This causes the slide to be horizontally released from the carousel and onto the belt to provide for the specimen to be traveling in a downward position. A roller 52 is located adjacent to the carousel to ensure that the slide in secured on the belt as it is released from the storage device.

While traveling on the first pair of conveyor belts, the slide will contact a microswitch (not illustrated). This microswitch will initiate the count of the individually transferred slides as each slide engages onto the first belts prior to the staining process.

The slide is then transported from the first pair of belts to the second pair of belts to permit for the rods or pips from the second pair of belts to aid in the transportation of the slide by driving it to the various processing stations.

A second motor (stepper motor) 54 is utilized to control and activate the first and second pairs of conveyor belts. This will provide for the slides to move at a constant rate of motion over the staining stations. The slide transport apparatus further includes an override switch for disengaging the stepper motor and stopping the movement of the slide transport apparatus when an alarm condition has been detected.

The first platen of the automated slide staining system includes staining stations 18 having an unique design and configuration. As illustrated in the figures (FIGS. 1 and 2), located at the corner of each station is an aperture 56. These apertures 56 allow for a staining fluid to be dispensed in a capillary form between the underside of the slide and the upper surface of each staining station.

As further illustrated, the stations are configured to be on the first platen at an acute angle. This acute angle aids in the flow of the staining fluid on the slide and also aids in the removal of the chemical as the slide is leaving the respective station.

The first platen further includes a plurality of troughs 58, which are situated between each station, and reservoirs (not illustrated), which are located in the front of the staining stations. A drainage orifice (not illustrated) is located within each reservoir. A waste tank (not illustrated) is underneath the first platen. This arrangement provides for the excess staining fluid from each station to flow into the troughs and to the reservoir. From the reservoir, the excess fluid flows into the waste tank via the drainage orifices. The waste tank can easily be removed from the housing via a first door 60. A display window 62 which is located on the front of the slide staining system, alerts the operator to empty and disposed of the fluid in the waste tank once a certain number of slides (i.e. 500) have been processed. The combination of the station being situated at acute angles and the location of the troughs provides for the staining fluid from the preceding station not to carry over to the succeeding station.

The last dispensing station 18a of the staining system dispenses a resin solution onto the slide. Adjacent to the last station is a heating station. After the resin solution has been dispensed onto the slide, it will travel to the heating station. The heating station consists of a convector 64 which will enable the resin solution to dry so that the tissue specimen, located on the slide, will be sealed. This seal creates a protective coating so that the specimen will be in a sterile and contaminant free environment.

From the heating station, each slide is directed to a slide receptacle 66. This slide receptacle receives and maintains the slides after a complete traverse of the slide staining stations.

The automated slide staining system also includes a fume extractor. The fume extractor removes the toxic fumes generated by the staining fluids during the dispensing cycle. The fume extractor consists of a plurality of openings 68, located above the staining stations, a charcoal filter within a housing 70, and an exhaust 72 having an exhaust fan. A cover or hood 74 is located above the staining stations in order to trap the fumes from the staining solutions. This will enable them to be extracted from the area of the staining stations by way of the plurality of the openings 68. The charcoal filter absorbs the toxic fumes from the staining solution, while the exhaust fan which is controlled by a third motor 76, disposes the purified fumes from the automated slide staining system via the exhaust 72.

The charcoal filter can be remove and replaced simply by opening a second door 78 on the housing. This second door exposes the filter's housing 70 and permits for it to be open so that the filter can be removed and/or replaced.

The staining fluid used in the automated slide staining system travels to its respective station via polytetraflouroethlyene (PTFE or TEFLON) transfer tubings 80. Each tube consists of a first end and a second end. The first end is inserted to the underside of the staining station and into the aperture. The second end is attached to a cannula tube 82.

Figure 4:
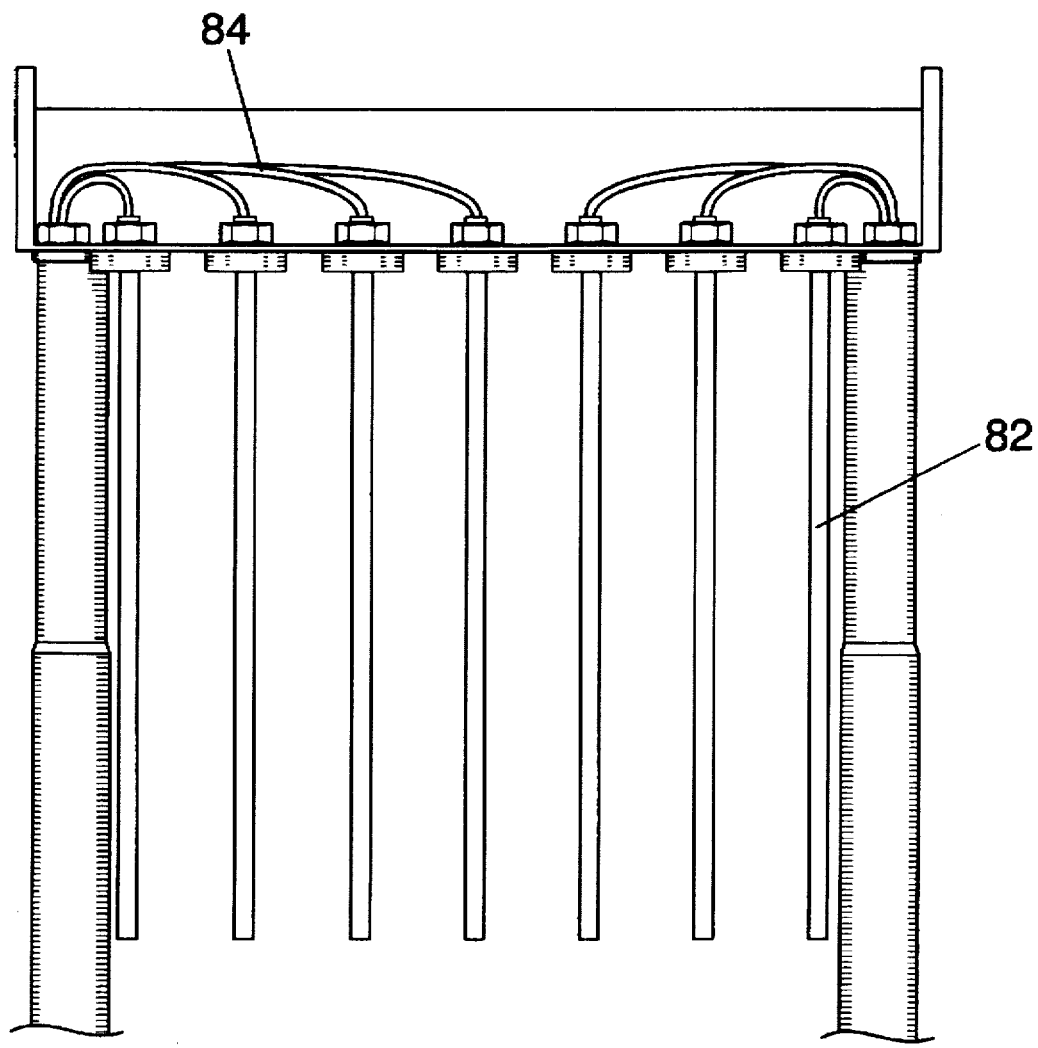
FIG. 4 is a front view of the cannula tubes used in the staining system of the present invention.

The cannula tubes 82 as illustrated in FIG. 2 and as further illustrated in FIG. 4 are inserted into a plurality of containers 84 containing a staining fluid. These tubes are connected to a pump 86 to permit for the staining fluid to flow from the cannula tube 82 to the aperture of the staining station via the transfer tubing 80. The pump is controlled by a fourth motor (illustrated but not labeled). The combination of the cannula tubes and the transfer tubing is also referred to as a channel. Each tubing is connected to a solenoid valve 88. The valve 88 controls the directional flow of the fluid. When the valve is in a closed position, the fluid is recirculating within the channel, while when the valve is in an open position, the fluid is diverted to the aperture within a station. When a slide is over the aperture of a particular station, a microprocessor activates the valve, for that particular station, to an open position. This will divert the fluid and provide for that fluid to be dispensed onto the particular station.

The second motor (stepper motor) is utilized for actuating the conveyor belts in order to guide the slides along the first platen of the staining system. A microprocessor (located within the electric bay 90) is used to count the steps or distance that each slide travels. When a slide reaches a particular and predetermined distance, the microprocessor will activate the solenoid valve so that the staining fluid for a particular station can be diverted to that station. The solenoid valve will remain open until the slide has traveled a certain or predetermined distance, at which time the microprocessor will send a signal to close the solenoid valve. This closure of the solenoid valve will provide for the fluid to recirculate within its respective channel.

Figure 5:
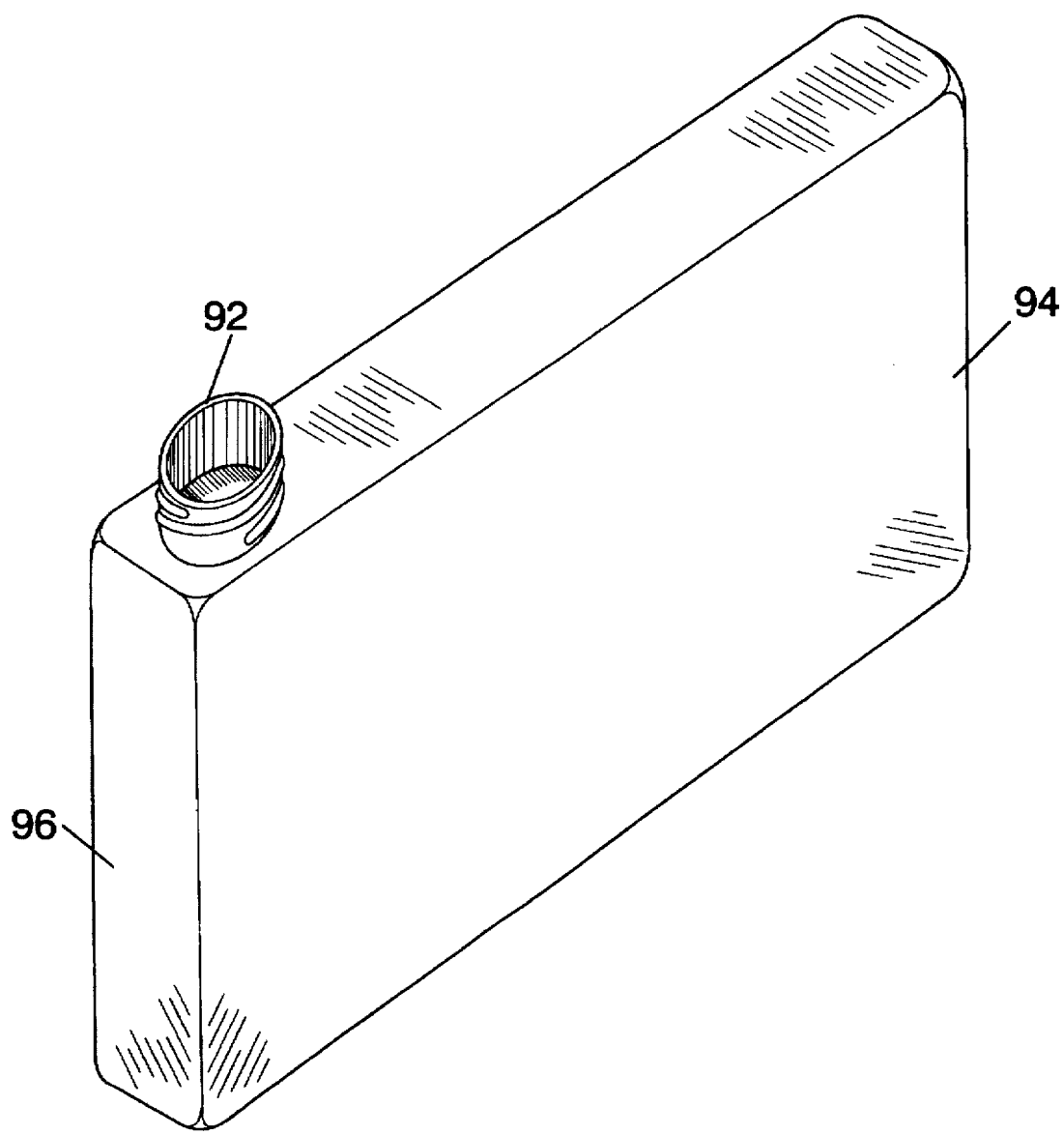
FIG. 5 is a perspective view of a bottle which is used to hold the staining fluids used in the automated slide staining system of the present invention.

The containers used for storing the respective staining fluids are provided with a unique shape and design. As illustrated in FIG. 5, each of the staining bottles includes an aperture 92 for receiving the cannula tube and two side walls 94, which are substantially longer than the front wall 96 and rear wall (not shown). The containers are placed in a box to provide for contact to be made with the container side walls (see FIG. 2). This box is placed within the housing via a third door 98 (see FIG. 1) of the automated slide staining system 10. This arrangement permits for the installation and replacement of the staining fluids to be made quickly and efficiently by removing the box holding the plurality of containers.

As illustrated in the various views of the automated slide staining system (FIGS. 1 and 2), the four digit LED display window 62 is located above the first platen 16. Located in the proximity of the display window 62 is a plurality of keys or buttons 100. The keys or buttons represent the number of slides which are being processed in a particular batch 106, the speed of which the slides are traveling 104, and the number of slides which can be processed by utilizing the remaining staining fluid located in the containers 102. The four digit LED display window will enable an operator to display the desired key indication.

The speed at which the slides travel can be adjusted by the utilization of the speed button 104. This speed button will not only display the speed at which the slides are traveling, but will also permit the user to alter the speed. This change of speed will alter the intensity and contrast of the stain with respect to the tissue specimen.

In order to utilize the automated slide staining system of the present invention, an operator inserts stained slides into the compartments 38 of a storage device or carousel 12. The slides are secured in the storage device by springs 40 which are located inside each storage compartment.

The storage device is removably secured to a shaft. Once secured, the operator can then activate the power supply 108 of the staining system 10 by using a button to provide for the shaft to rotate, inherently causing the storage device 12 to rotate. The activation of the system will also initiate the conveyor belts 42 and 44.

The rods or pips 50 on the belts push or force a slide to exit the storage container 12. The slide is released from the storage container so that the specimen is facing in a downward position. The second motor 54 is used to control and operate the conveyor belts. The use of the first and second motors (stepper motors) and the arrangement and spacing of the rods or pips will permit for the slides to be released one at a time.

After release from the storage device, the slide first contacts a microswitch. The microswitch initiates the count of the individually transferred slide. After contact with the microswitch the slide is transferred to the staining stations 18 via the second set of conveyor belts 44.

The pulses that the microprocessor uses to drive a second motor 54 which powers the second set of conveyor belts are used to determine when the microprocessor will activate the solenoid valve for a particular station. Once a slide reaches a particular and predetermined distance, the microprocessor will transmit a signal to activate or open the solenoid valve of a particular station. This will enable the staining fluid to flow to the appropriate staining station. The solenoid valve will remain open until the slide has traveled a certain or predetermined distance, at which time the microprocessor will send a signal to close the solenoid valve.

The particular distance in this system for activation of the solenoid valve occurs when the slide is directly above the aperture in the station. The particular distance in which a signal will be transmitted to deactivate the system will occur when the slide exits that particular station.

The processing of the slides is continued until the slide reaches the heating station which includes the convector 64. At this time the resin coating, which was applied at the last dispensing station 18a, is dried. This will provide for the slide to have a protective resin coating. After the resin has dried, the slide will be transported and dropped into a slide receptacle 66.

The automated slide staining system will continue to release the slides from the storage device. This will continue until all the slides have been released or if there is not a sufficient amount of staining fluid to process the slides.

Figure 6:
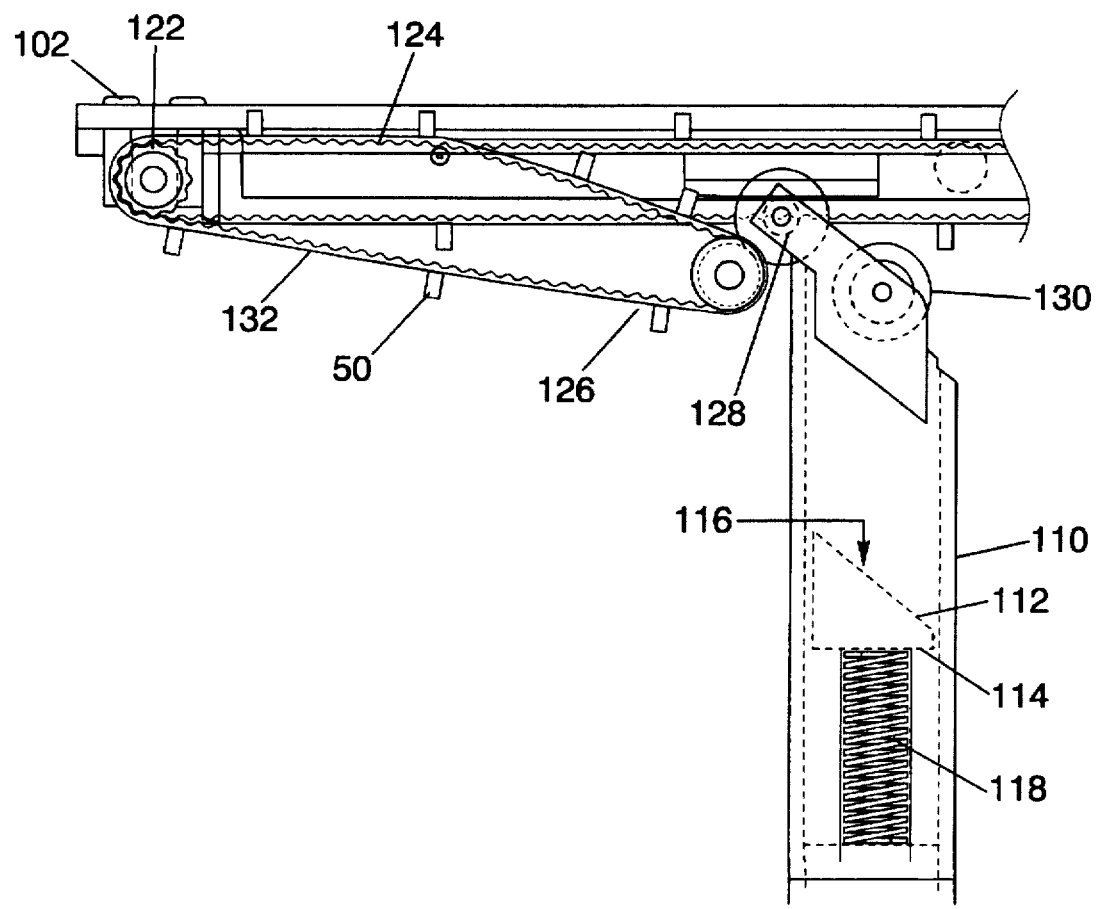
FIG. 6 is an enlarged view of the cover slip apparatus used in the second embodiment of the present invention.

In the above-described embodiment, a heating unit is provided after the last dispensing station. However, the automated slide staining system can be arranged such that a cover slip can be dispensed, one at a time, in order to apply it on a slide. FIG. 6 illustrates an enlarged view of the cover slip apparatus. As seen in this figure of the second embodiment, the cover slip apparatus includes a receptacle 110 which holds and maintains the cover slips. Internally located in the receptacle is a platform 112 (illustrated in outline). This platform includes a bottom planar surface 114 while the top 116 is provided with a surface having an obtuse angle with respect to the bottom planar surface. This angle will permit an easy removal of the cover slip from the receptacle. A spring 118 is situated under the platform to allow for the cover slips to be spring loaded within receptacle.

A second platen 120 is located in the proximity of the receptacle. The second platen includes a first end 122, a middle area 124, and a second end 126. The second end of the second platen is at an obtuse angle with respect to the middle area. The second end faces the receptacle which houses the cover slips. The middle portion to the first end of the second platen is linear with respect to the first platen 16. The middle area of the second platen is in the proximity of the first platen. A third pair of conveyor belts 132 are located on the edge the second platen. Extending vertically and outwardly from these belts are a plurality of evenly spaced rods or pips 50.

A first motor attached to a first roller 128 and a second motor attached to a second roller 130 are located between the platen and receptacle. This first roller is parallel to the second roller. The second roller will remove a cover slip from the receptacle, while the first roller guides the cover slip onto the second platen. The rods or pips enable the cover slips to travel along the second platen.

The activation of the automated slide staining system will provide for the third set of conveyor belts to be activated.

The utilization of the second embodiment of the present invention is similar to the first embodiment, except that in this embodiment the heating station is replaced with a cover slip unit. In this embodiment, the processing of the slides is continued until the slide reaches the cover slip apparatus. At this time the resin coating, which was applied at the last dispensing station, acts as an adhesive for the cover slip.

As the slide comes into the cover slip area, a sensor detects its presence and permits for the microprocessor to activate the first and second motors. This will permit for the first and second rollers to rotate. The rotation of the second roller will remove a cover slip from the receptacle. The first roller will guide the cover slip onto the second platen. The rods or pips from the third set of conveyor belts, will transport the cover slip along the second platen. As the cover slip surfaces from the first end to the middle area, the edges of the slide and cover slip will contact. This contact will occur at an angle of approximately 45 degrees. A pressure roller is located above the second platen and applies a sufficient amount of force on the slide to ensure the cover slip adheres to the slide. After the cover slip is completely secured to the slide, it will be transported to a holding receptacle via the second platen in combination with its respective conveyor system.

The automated slide staining system will continue to release the slides from the storage device. This will continue until all the slides have been released or if there is not a sufficient amount of staining fluid to process the slides.

This second embodiment further includes a second sensor. The second sensor detects when the cover slip receptacle is empty. If the cover slip receptacle is empty, a warning will be displayed on the front panel of the LED display window.

It is noted that the size of each station and the number of stations used in the first or second embodiment can be changed in order to accommodate the testing that is desired (i.e. histology versus cytology).

The method involved in the processing of a histology tissue specimen using the automated slide staining system of the present invention includes a plurality of different solutions to be dispensed at each station. At the first station, the paraffin is removed from the tissue by the use of xylene. The specimen is then hydrated with ABS alcohol (second station) followed by a hydration of diluted alcohol (third station). The cell nuclei of the specimen is then treated with a hematoxylin compound (fourth station). The next step is to remove the excess stain from the specimen using a diluted acid compound (fifth station). The specimen is dehydrated by using a pure alcohol (sixth station). The enhancing of the nuclear stain contrast with respect to the specimen using a dilute alkali solution (seventh station). The specimen is then dehydrated by the use of pure alcohol (eight station) The specimen is then stained for cytoplasm by using an eosin compound (ninth station). Again the specimen is dehydrated, this time by the use of ABS alcohol (tenth station). Further dehydration of the specimen occurs with more ABS alcohol (eleventh station). The specimen is cleaned using a xylene solution (twelfth station). At the last dispensing station, a coating is applied to the slide for maintaining the specimen to be in a contamination free status (thirteenth station).

From the last dispensing station, the slide is either transported to a drying station or to a cover slip area.

The method involved in the processing of a cytology tissue specimen using the automated slide staining system of the present invention includes a plurality of different solutions to be dispensed at each station. At the first station, the specimen is hydrated with an alcohol solution. The specimen is hydrated again with a second alcohol solution (second station). The plurality of cell nuclei of the tissue specimen is processed with a hematoxylin stain compound (third station). Excess staining material is then removed from the specimen with a diluted acid solution (fourth station). The specimen is dehydrated with an alcohol solution (fifth station). The next step is for enhancing the nuclear staining contrast of the tissue specimen with a dilute alkali solution (sixth station). The specimen is dehydrated with an alcohol solution (seventh station). The next step is to counterstain the specimen for highlighting cytoplasmic cell material (eighth station). The removal of the excess staining material from the tissue specimen is the next step (ninth station). Counterstaining the specimen for cytoplasmic cell contrast then occurs (tenth station). The specimen is then dehydrated with ABS alcohol (eleventh station). Further dehydration of the specimen occurs with a second dispensing of ABS alcohol (twelfth station). The specimen is then cleaned with a xylene compound (thirteenth station). At the last dispensing station, a coating is applied to the slide for maintaining the specimen to be in a contamination free status (fourteenth station).

From the last dispensing station, the slide is either transported to a drying station or to a cover slip area.

While the invention has been particularly shown and described with reference to an embodiment thereof, it will be understood by those skilled in the art that various changes in form and detail may be made without departing from the spirit and scope of the invention.

I claim:

1. An automated slide staining system comprising in combination:
    a slide storage device for holding a plurality of slides with each slide having a tissue specimen thereon, the slide storage device being acurate in shape and having a horizontally disposed central axis, the slide storage device further having a plurality of radially oriented walls for forming a plurality of compartments, each compartment for holding a slide for subsequent individual transfer;
    a plurality of slide staining stations offset from the slide storage device and being horizontally disposed in a single file relationship for urging sequential capillary communication with each transferred slide, each staining station further having an aperture for dispensing a staining fluid into a capillary formed between an underside of the slide and upper surface of each staining station;
    a slide receptacle for receiving a stained slide after a complete transverse of the slide staining stations;
    a slide transport apparatus therebetween, the apparatus being adapted for receiving and removing an individual unstained slide from the compartment and further, for transporting the unstained slide horizontally on a belt for urging approximate capillary communication between an underside of each slide and an upper surface of each staining station;
    a plurality of containers for storing the respective staining fluids, each container being in hydraulic communication with a cannula tube for urging withdrawal by the cannula tube, each container further being box-like in shape for forming a rectangular carton for urging easy changing of the staining fluids after a preselected number of slides have been stained;
    an exhaust fan disposed rearwardly and adjacent to the slide transport apparatus for removing fumes generated by the staining fluids during the dispensing cycle; and
    the slide transport apparatus further includes a speed controller to vary the time a slide takes to traverse each staining station for changing the intensity and contrast of the stain with respect to the tissue specimen.

2. An automated slide staining system as recited in claim 1 and further including a heating station on an end remote from the slide storage device and adjacent to a last staining station for drying the tissue specimen on the underside of the slide after all the staining fluids have been applied to the specimen.

3. An automated slide staining system as recited in claim 1 wherein the slide transport apparatus further includes a microswitch to initiate the count of the individually transferred slides as each slide engages the belt prior to the staining process.

4. An automated slide staining system as recited in claim 1 wherein the slide transport apparatus further includes a drive motor for urging the slide to move at a constant rate of motion over the staining stations and an override switch for disengaging the drive motor and stopping the movement of the slide transport apparatus when an alarm condition has been detected.

5. An automated slide staining system as recited in claim 1 wherein the slide transport apparatus further includes a display window for indicating the number of slides to be processed, the amount of staining fluid remaining in the containers, the number of slides processed, and the speed at which the slides are traveling over the staining stations, the display window further being in electronic communication with a microprocessor for receiving a plurality of electric signals to indicate the current status of the process variables during the staining process and the number of slides process.

6. An automated slide staining system as recited in claim 4 wherein the drive motor further includes a plurality of stepper motors in synchronized communication with the microprocessor for maintaining consistent timely passage of the slides over each staining station and the heating station, and further for urging synchronized discharge of the staining fluids onto the slide as each slide passes over each respective staining station in capillary communication.

7. An automated slide staining system as recited in claim 1 and further including a waste tank receptacle oriented below the bed of the slide staining transport apparatus in draining communication for receiving excess staining fluids during the staining process, the waste tank receptacle being adapted for electronic communication with the microprocessor for alarming the operator when the receptacle has reached a full level.

8. An automated slide staining system as recited in claim 1 and further including a pump, a plurality of valves, and a plurality of transfer tubing in hydraulic communication with the cannula tubes for urging fluid flow from each staining fluid container to the aperture on the upper side of one of the staining stations.

9. An automated slide staining system as recited in claim 8 wherein the pump and the plurality of valves are in electric communication with the microprocessor for urging synchronized discharge of the staining fluid when a slide is in capillary communication with each staining station.

10. An automated slide staining system as recited in claim 1 for staining histology specimens.

11. An automated slide staining system as recited in claim 1 for staining cytology specimens.

12. An automated slide staining system as recited in claim 1 wherein the slide storage device further includes a plurality of slide retainer springs, each spring being oriented between two adjacent walls for urging releasable retention of the slide within the compartment.

13. An automated slide staining system as recited in claim 2 wherein the slide transport apparatus further includes a resin dispensing station, the resin dispensing station being coplanar with the plurality of staining stations and oriented between the last staining station and the heating station for applying a resin material to the stained tissue specimen, the resin material for coating the tissue specimen and maintaining the specimen in a sterile, contaminant free environment.

14. An automated slide staining system as recited in claim 1 and further including a cover slip storage and dispensing apparatus on an end remote from the slide storage device and adjacent to a last staining station, the cover slip storage and dispensing apparatus further including a cover slip storage device for holding a plurality of cover slips, the cover slip storage device having a rectangular box-like shape,
 a platen including a slide transport apparatus being adapted for receiving and directing an individual cover slip from the cover slip storage device to a processed stained slide for urging the cover slip to come into contact with the processed stained slide; and
 a cover slip removing mechanism located between the cover slip storage device and the platen for enabling the cover slip to be removed from the cover slip storage device and onto the second platen.

15. An automated slide staining system as in claim 14 and further including a platform internally located in the cover slip storage device, the platform having a bottom planar surface and a top further having an obtuse angle with respect to the bottom planar surface, and a spring is disposed under the bottom planar surface in resilient communication with the cover slips in the cover slip storage device.

16. An automated slide staining system as recited in claim 15 wherein the cover slip further includes removing mechanism consists of a first motor attached to a first roller and a second motor attached to a second roller, for removing a single cover slip from the cover slip storage device with the first roller and for placing the single cover slip onto the second platen with the second roller.

17. An automated slide staining system as recited in claim 16 wherein the cover slip storage and dispensing apparatus further includes a first sensor and a second sensor;
 the first sensor detects a presence of the processed stained slide and permits a microprocessor to activate the first motor and the second motor and initiates the first roller and the second roller; and
 the second sensor detects when the cover slip storage device is empty.

18. An automated slide staining system as recited in claim 17 and further including a pressure roller disposed above the second platen for applying a force for maintaining surface communication between the slide and the cover slip.

19. An automated slide staining system as recited in claim 14 wherein the slide transport apparatus further includes a resin dispensing station, the resin dispensing station being co-planar with the plurality of staining stations and oriented between the last staining station and the cover slip storage and dispensing apparatus for applying a resin material to the stained tissue specimen.

20. An automated slide staining system as recited in claim 1 wherein the slide transport apparatus further includes a bed offset and underneath the apparatus for supporting the plurality of staining stations, the bed having a plurality of drainage orifices for removing excess staining fluid during the staining process at each staining station.

21. An automated slide staining system as recited in claim 1 wherein the belt further includes a plurality of paired spaced-apart vertically disposed rods, each pair of rods for removing the individual slide from one of the compartments on the slide storage device and being adapted for transporting each individual slide across each successive staining station in approximate capillary communication only.

22. An automated slide system as in claim 21 wherein each container for storing the respective staining fluids further includes a pair of sidewalls in a spaced apart relationship and a pair of front walls in a spaced apart relationship, the side walls having a length longer than the front walls for forming an elongated longitudinal container with a shorter cross-sectional transverse width.

23. An automated slide staining system comprising in combination:
 a slide storage device for holding a plurality of slides with each slide having a tissue specimen thereon, the slide storage device is removably secured to the slide staining system via a removable securing means, the slide storage device includes a plurality of compartments, each compartment is for holding a slide for subsequent individual transfer and for prohibiting a preceding slide from contacting a succeeding slide;
 a plurality of slide staining stations offset from the slide storage device and being horizontally disposed in a single file relationship for urging sequential capillary communication with each transferred slide, each staining station further having an aperture for dispensing a staining fluid into a capillary formed between an underside of the slide and upper surface of each staining station;
 a slide receptacle for receiving a stained slide after a complete transverse of the slide staining stations;
 a slide transport apparatus therebetween, the apparatus being adapted for receiving and removing an individual unstained slide from the compartment and further, for transporting the unstained slide horizontally on a belt for urging approximate capillary communication between an underside of each slide and an upper surface of each staining station;
 a plurality of containers for storing the respective staining fluids, each container being in hydraulic communication with a cannula tube for urging withdrawal by the cannula tube; and
 the slide transport apparatus further includes a speed controller to vary the time a slide takes to traverse each staining station for changing the intensity and contrast of the stain with respect to the tissue specimen.

24. An automated slide staining system as in claim 23 wherein an exhaust fan is disposed rearwardly and adjacent to the slide transport apparatus for removing fumes generated by the staining fluids during the dispensing cycle.

25. An automated slide staining system as in claim 23, further including a cover slip storage and dispensing apparatus on an end remote from the slide storage device and adjacent to a last staining station.

26. An automated slide staining system as in claim 23 and further including a heating station on an end remote from the slide storage device and adjacent to a last staining station for drying the tissue specimen on the underside of the slide after all the staining fluids have been applied to the specimen.

27. An automated slide staining system as recited in claim 26 wherein the slide transport apparatus further includes a resin dispensing station, the resin dispensing station being coplanar with the plurality of staining stations and oriented between the last staining station and the heating station for applying a resin material to the stained tissue specimen, the resin material for coating the tissue specimen and maintaining the specimen in a sterile, contaminant free environment.

28. An automated slide staining system comprising in combination:

a slide storage device for holding a plurality of slides with each slide having a tissue specimen thereon;

a plurality of slide staining stations offset from the slide storage device and being horizontally disposed in a single file relationship for urging sequential capillary communication with each transferred slide, each staining station further having an aperture for dispensing a staining fluid into a capillary formed between an underside of the slide and upper surface of each staining station;

a slide transport apparatus therebetween, the apparatus being adapted for receiving and removing an individual unstained slide from the slide storage device and further, for transporting the unstained slide horizontally on a belt for urging approximate capillary communication between an underside of each slide and an upper surface of each staining station;

a plurality of containers for storing the respective staining fluids, each container being in hydraulic communication with a cannula tube for urging withdrawal by the cannula tube;

a last station dispenses an adhesive substance;

a cover slip storage and dispensing apparatus on an end remote from the slide storage device and adjacent to the last staining station for enabling a cover slip to be dispense onto the lower surface of a processed slide for securing the cover slip thereto, the cover slip storage and dispensing apparatus including a receptacle for holding and storing a plurality of cover slips, a removing means for removing the cover slip from the receptacle, and an engaging means for enabling the cover slip to engage and contact the lower surface of the processed slide; and the slide transport apparatus further includes a speed controller to vary the time a slide takes to traverse each staining station for changing the intensity and contrast of the stain with respect to the tissue specimen.

* * * * *